United States Patent
Holla et al.

(10) Patent No.: US 7,544,809 B2
(45) Date of Patent: Jun. 9, 2009

(54) METHOD FOR THE PREPARATION OF OXAZOLES BY CONDENSING AROMATIC ALDEHYDES WITH α-KETOXIMES TO FORM N-OXIDES AND REACTING SAME WITH ACTIVATED ACID DERIVATIVES

(75) Inventors: Wolfgang Holla, Kelkheim (DE); Rolf-Ludwig Hoerlein, Frankfurt (DE); Berndt Kulitzscher, Esselbach (DE); Wolfgang Laux, Sceaux (FR); Thomas Stuedemann, Kelkheim (DE); Christoph Tappertzhofen, Frankfurt (DE); Robert J. H. Scheffer, Ingelheim (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 11/754,477

(22) Filed: May 29, 2007

(65) Prior Publication Data
US 2008/0058529 A1    Mar. 6, 2008

Related U.S. Application Data

(63) Continuation of application No. PCT/EP2005/012800, filed on Dec. 1, 2005.

(30) Foreign Application Priority Data
Dec. 15, 2004   (DE) .................. 10 2004 060 227

(51) Int. Cl.
*C07D 263/32* (2006.01)

(52) U.S. Cl. ...................................... 548/235
(58) Field of Classification Search .................. 548/235
See application file for complete search history.

(56) References Cited

U.S. PATENT DOCUMENTS 5,036,079 A * 7/1991 Clark et al. .................. 514/333

FOREIGN PATENT DOCUMENTS

| WO | WO 02/16332 | 2/2002 |
| WO | WO 02/100403 | 12/2002 |
| WO | WO 2004/075815 | 9/2004 |
| WO | WO 2004/076426 | 9/2004 |

OTHER PUBLICATIONS

Palmer et al. The Chemistry of Heterocyclic Compounds vol. 60: Oxazoles: Synthesis, Reactions, and Spectroscopy, Part A, 2003 John Wiley & Sons, Inc.*

* cited by examiner

*Primary Examiner*—Rebecca L Anderson
*Assistant Examiner*—Jason Nolan
(74) *Attorney, Agent, or Firm*—Jiang Lin; Craig M. Bell

(57) ABSTRACT

The present invention is comprised of improved methods in the preparation of oxazoles which results in higher yields with less impurities and contaminants. Oxazoles constitute valuable intermediates in the synthesis of pharmaceutically active substances such as, for example peroxisome proliferator activated receptor (PPAR) agonists which are pharmaceutical actives which can have a positive influence on both lipid and glucose metabolism.

11 Claims, No Drawings

US 7,544,809 B2

METHOD FOR THE PREPARATION OF OXAZOLES BY CONDENSING AROMATIC ALDEHYDES WITH α-KETOXIMES TO FORM N-OXIDES AND REACTING SAME WITH ACTIVATED ACID DERIVATIVES

CROSS-REFERENCE TO RELATED APPLICATIONS

This application is a continuation of International Patent Application No. PCT/EP2005/012800 filed on Dec. 1, 2005 which is incorporated herein by reference in its entirety which also claims the benefit of priority of German patent application Ser. No. 10/2004 060 227.1 filed on Dec. 15, 2004.

FIELD OF THE INVENTION

The invention relates generally to chemical processes the compounds produced thereby and more specifically, processes for the preparation of pharmaceutical actives and intermediates thereof for the regulation of lipid and/or glucose metabolism. The compounds are also useful in the subsequent treatment of disorders thereof. More specifically, the present invention is comprised of improved methods in the preparation of oxazoles which results in higher yields with less impurities and contaminants. Oxazoles constitute valuable intermediates in the synthesis of pharmaceutically active substances such as, for example peroxisome proliferator activated receptor (PPAR) agonists.

BACKGROUND OF THE INVENTION

The invention allows the preparation of oxazoles in high yield and great purity. Oxazoles constitute valuable intermediates in the synthesis of pharmaceutically active substances, for example PPAR agonists. Appropriate examples of PPAR agonists are described, inter alia, in WO 03/020269, WO 2004/075815, WO 2004/076447, WO 2004/076428, WO 2004/076426, WO 2004/076427, DE 102004039533.0, DE 102004039532.2, DE 102004039509.8. The latter are pharmaceutical actives which can have a positive influence both on lipid metabolism and on glucose metabolism.

pharmaceutical actives which can have a positive influence both on lipid metabolism and on glucose metabolism.

The condensation of aromatic aldehydes with α-ketoximes to give N-oxides and the subsequent reaction with activated acid derivatives to give oxazoles is known per se.

For the conversion of the N-oxides to the oxazoles, the literature describes the reagents phosphorus (III) chloride ($PCl_3$) and phosphorus oxychloride ($POCl_3$) and, in one variant, acetic anhydride (($CH_3COO)_2O$) (Y. Goto, M. Yamazaki, M. Hamana, Chem Pharm Bull. 19 (1971) 2050, and literature cited there). These reagents are not widely applicable and often lead to no products or to highly contaminated products which can only be obtained in sufficient purity with low yields in a costly and inconvenient manner, for example by chromatographic processes.

The reaction conditions described require the isolation of the N-oxides. For N-oxides with exothermic decomposition potential, this constitutes a considerable safety risk and prevents the process from being practiced on the industrial scale.

It has now been found that, surprisingly, the transformation of the N-oxides to the halomethyloxazoles proceeds unexpectedly smoothly with high yield and great purity with inorganic thionyl halides or organic sulfonyl halides.

Although it was unexpected on the basis of the remarks in the literature, halomethyloxazoles in some cases precipitate cleanly directly out of the reaction mixture in the form of the free base or as salts.

Unexpectedly, for N-oxides with exothermic decomposition potential, it has been possible to achieve both safe preparation in dilute solution and the further direct reaction of the solution to give the halo-methyloxazoles.

SUMMARY OF THE INVENTION

The invention relates to a process for the preparation of oxazoles by the condensation of aldehydes with α-ketoximes to give N-oxides in the form of their salts or as free bases. These compounds are then subsequently reacted with activated acid derivatives to give oxazoles in the form of their salts or as free bases. More specifically, the present invention comprises a condensation reaction between aromatic aldehydes and α-ketoximes followed by the reaction of inorganic thionyl halides or organic sulfonyl halides to produce higher, purer yields of chloromethyloxazoles.

DETAILED DESCRIPTION OF THE INVENTION

The present invention comprises an improved process for the preparation of compounds of formula IV by means of conversion of aromatic aldehydes of the formula I using α-ketoximes of the formula II via N-oxides of the formula III to produce the halomethyloxazoles of the formula IV,

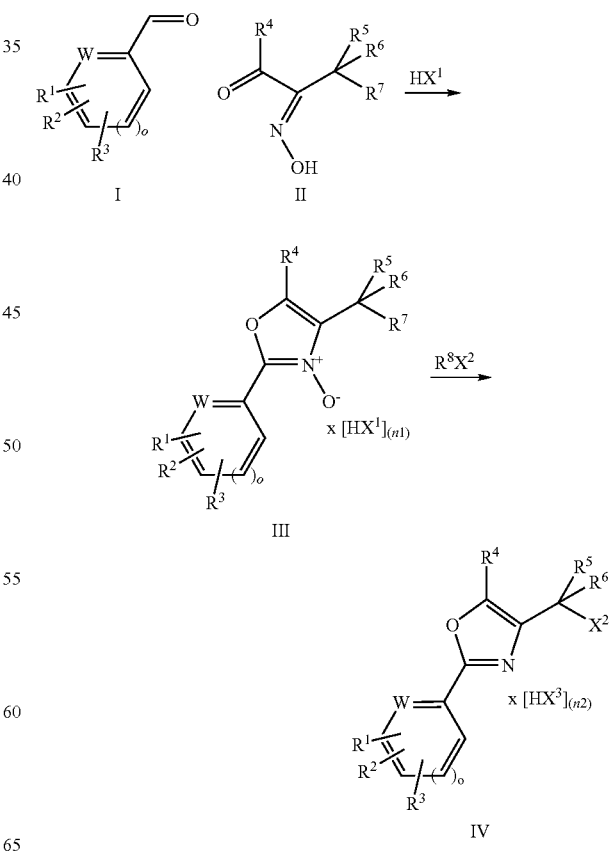

which comprises converting the aromatic aldehydes of the formula I using the α-ketoximes of the formula II

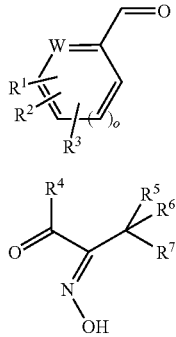

in which:

R$^1$ is selected from the group consisting of H, (C1-C6)-alkyl, F, Cl, Br, I, O—(C0-C8)-alkylene-H, CF$_3$, OCF$_3$, SCF$_3$, SF5, OCF$_2$—CHF2, (C6-C10)-aryl, O—(C6-C10)-aryl, O—(C1-C4)-alkylene-(C6-C10)-aryl, NO2, COOR$^9$, CONR$^{10}$R$^{11}$, SH, or NR$^{10}$R$^{11}$, wherein aryl is unsubstituted or mono-, di- or tri-substituted by F, Cl, Br, I, (C1-C4)-alkyl, O—(C1-C4)-alkyl or CF$_3$;
wherein
R$^9$ is selected from the group consisting of H, Li, Na, K, ½ Mg, ½ Ca, ammonium ions which are unsubstituted or mono-, di- or tri-substituted by (C1-C4)-alkyl, or is (C1-C8)-alkyl,
R$^{10}$ and R$^{11}$ are each independently selected from the group consisting of H, (C1-C5)-alkyl, phenyl or CH$_2$-phenyl, wherein phenyl is unsubstituted or mono-, di- or trisubstituted by F, Cl, Br, I, (C1-C4)-alkyl, O—(C1-C4)-alkyl or CF$_3$;
or
R$^{10}$ and R$^{11}$ together are (C4-C5)-alkylene, wherein one CH$_2$ group may be replaced by O, S, NH, N—CH$_3$ or N-benzyl;
R$^2$ is selected from the group consisting of H, (C1-C6)-alkyl, F, Cl, Br, I, O—(C0-C8)-alkylene-H, CF3, OCF3, SCF3, SF5, OCF$_2$—CHF2, (C6-C10)-aryl, O—(C6-C10)-aryl, O—(C1-C4)-alkylene-(C6-C10)-aryl, NO$_2$, COOR$^9$, CONR$^{10}$R$^{11}$, SH, or NR$^{10}$R$^{11}$, wherein aryl is unsubstituted or mono-, di- or tri-substituted by F, Cl, Br, I, (C1-C4)-alkyl, O—(C1-C4)-alkyl and CF$_3$; and
wherein R$^9$, R$^{10}$ and R$^{11}$ are each as defined above;
R$^3$ is selected from the group consisting of H, (C1-C6)-alkyl, F, Cl, Br, I, O—(C0-C8)-alkylene-H, CF3, OCF3, SCF3, SF5, OCF2-CHF2, (C6-C10)-aryl, O—(C6-C10)-aryl, O—(C1-C4)-alkylene-(C6-C10)-aryl, NO$_2$, COOR$^9$, CONR$^{10}$R$^{11}$, SH, or NR$^{10}$R$^{11}$, where aryl is unsubstituted or mono-, di- or trisubstituted by F, Cl, Br, I, (C1-C4)-alkyl, O—(C1-C4)-alkyl or CF$_3$;
where R$^9$, R$^{10}$ and R$^{11}$ are each as defined above; and
W is CH or N, if o=1;
W is O, S or NR12, if o=0;
o is 0 or 1;
R12 is selected from the group consisting of H, (C1-C6)-alkyl, (C1-C6)-alkylenephenyl, phenyl;
R$^4$ is selected from the group consisting of H, (C1-C8)-alkyl, (C3-C8)-cycloalkyl, (C1-C3)-alkylene-(C3-C8)-cycloalkyl, phenyl, (C1-C3)-alkylenephenyl, (C5-C6)-heteroaryl, (C1-C3)-alkylene-(C5-C6)-heteroaryl or (C1-C3)-alkyl which is fully or partly substituted by F, or COOR$^9$, CONR(10)R(11);
wherein R$^9$, R$^{10}$ and R$^{11}$ are each as defined above;
R$^5$ and R$^6$ are each independently selected from the group consisting of (C1-C8)-alkyl, F, Cl, Br, I, O—(C0-C8)-alkylene-H, O—(C6-C10)-aryl, O—(C1-C4)-alkylene-(C6-C10)-aryl, COOR$^9$, CONR$^{10}$R$^{11}$, SH and NR$^{10}$R$^{11}$,
wherein R$^9$, R$^{10}$, R$^{11}$ are each as defined above;
or,
R$^5$ and R$^6$ together are selected from the group consisting of (C4-C5)-alkylene, in which one —CH$_2$ group may be replaced by O, S, NH, N—CH$_3$ or N-benzyl;
R$^7$ is selected from the group consisting of is H or (C1-C8)-alkyl;
in the presence of one or more acids HX$^1$ selected from the group consisting of HCl, HBr, H$_2$SO$_4$, H$_3$PO$_4$, HOOCCF3, HOOCCCl$_3$, HO$_3$SCF$_3$, HO$_3$SCH$_3$, HO$_3$SC$_6$H$_5$, HO$_3$S—C$_6$H$_4$-p-CH$_3$, HOOCH,
to the N-oxides of the formula III

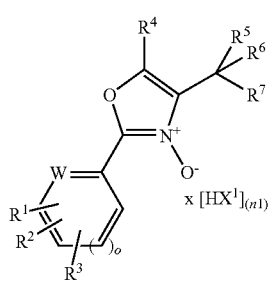

in which R$^1$, R$^2$, R$^3$, R$^4$, R$^5$, R$^6$, R$^7$ and X$^1$ are each as defined above and
n1 is 0, 1, ½ or ⅓;
and wherein the latter is subsequently reacted with the reagent R$^8$X$^2$ which is a compound selected from the group consisting of:
SOCl—Cl, SOBr—Br, CH$_3$SO$_2$—Cl, CF3SO$_2$—CL, C$_6$H$_5$SO$_2$—Cl, p-CH$_3$—C$_6$H$_4$—SO$_2$—Cl, CH$_3$SO$_2$—O$_3$SCH$_3$, CF3SO$_2$—O$_3$SCF3, C$_6$H$_5$SO$_2$—O$_3$SC $_6$H$_5$ or p-CH$_3$—C$_6$H$_4$—SO$_2$—O$_3$S—C$_6$H$_4$-p-CH$_3$,
to give the halomethyloxazoles of the formula IV

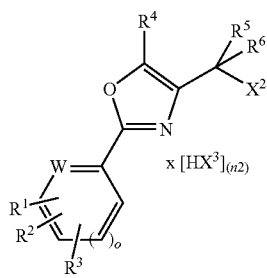

wherein R$^1$, R$^2$, R$^3$, R$^4$, R$^5$, R$^6$ and X$^2$ are each as defined above and
X$^3$ is Cl, Br, CH$_3$SO$_3$, CF3SO$_3$, C$_6$H$_5$SO$_3$ or p-CH$_3$—C$_6$H$_4$—SO$_3$ and
n2 is 0 or 1.

Preferably, the invention relates to a process for preparing the compounds of the formula IV in which:
W=CH and
o=1.

More preferably, the invention further relates to a process for preparing the compounds of the formula IV in which:
R1 is H;
$R^2$ is selected from the group consisting of H, (C1-C6)-alkyl, F, Cl, Br, I, O—(C0-C8)-alkylene-H, CF3, OCF3, SCF3, SF5, OCF2—CHF2, (C6-C10)-aryl, O—(C6-C10)-aryl, O—(C1-C4)-alkylene-(C6-C10)-aryl, NO2, COOR$^9$, CONR$^{10}$R$^{11}$, SH, or NR$^{10}$R$^{11}$, where aryl is unsubstituted or mono-, di- or trisubstituted by F, Cl, Br, I, (C1-C4)-alkyl, O—(C1-C4)-alkyl or CF3;
wherein
$R^9$ is selected from the group consisting of H, Li, Na, K, ½ Mg, ½ Ca, ammonium ions which are unsubstituted or mono-, di- or trisubstituted by (C1-C4)-alkyl, or is (C1-C8)-alkyl,
$R^{10}$ and $R^{11}$ are each independently is selected from the group consisting of H, (C1-C5)-alkyl, phenyl or CH$_2$-phenyl,
where phenyl is unsubstituted or mono-, di- or trisubstituted by F, Cl, Br, I, (C1-C4)-alkyl, O—(C1-C4)-alkyl or CF3; or
$R^{10}$ and $R^{11}$ together are (C4-C5)-alkylene, in which one CH$_2$ group may be replaced by O, S, NH, N—CH$_3$ or N-benzyl;
$R^3$ is selected from the group consisting of H, (C1-C6)-alkyl, F, Cl, Br, I, O—(C0-C8)-alkylene-H, CF3, OCF3, SCF3, SF$_5$, OCF2-CHF2, (C6-C10)-aryl, O—(C6-C10)-aryl, O—(C1-C4)-alkylene-(C6-C10)-aryl, NO2, COOR$^9$, CONR$^{10}$R$^{11}$, SH, or NR$^{10}$R$^{11}$, where aryl is unsubstituted or mono-, di- or trisubstituted by F, Cl, Br, I, (C1-C4)-alkyl, O—(C1-C4)-alkyl or CF3;

where $R^9$, $R^{10}$ and $R^{11}$ are each as defined above.

The invention even more preferably relates to a process for preparing the compounds of the formula IV in which:
$R^1$ is H;
$R^2$ is H;
$R^3$ is selected from the group consisting of H, (C1-C6)-alkyl, F, Cl, Br, I, O—(C0-C8)-alkylene-H, CF3, OCF3, SCF3, SF5, OCF2-CHF2, (C6-C10)-aryl, O—(C6-C10)-aryl, O—(C1-C4)-alkylene-(C6-C10)-aryl, NO2, COOR$^9$, CONR$^{10}$R$^{11}$, SH, or NR$^{10}$R$^{11}$, where aryl is unsubstituted or mono-, di- or trisubstituted by F, Cl, Br, I, (C1-C4)-alkyl, O—(C1-C4)-alkyl or CF3;
and wherein
$R^9$ is selected from the group consisting of H, Li, Na, K, ½Mg, ½Ca, ammonium ions which are unsubstituted or mono-, di- or trisubstituted by (C1-C4)-alkyl, or is (C1-C8)-alkyl,
$R^{10}$ and $R^{11}$ are each independently is selected from the group consisting of H, (C1-C5)-alkyl, phenyl or CH$_2$-phenyl,
Wherein if phenyl, the phenyl is unsubstituted or mono-, di- or tri-substituted by F, Cl, Br, I, (C1-C4)-alkyl, O—(C1-C4)-alkyl or CF3; or
$R^{10}$ and $R^{11}$ together are (C4-C5)-alkylene, in which one CH$_2$ group may be replaced by O, S, NH, N—CH$_3$ or N-benzyl.

The invention more preferably further relates to a process for preparing the compounds of the formula IV, in which:
$R^1$, $R^2$, $R^3$ are each independently selected from the group consisting of H, (C1-C6)-alkyl, F, Cl, Br, I, O—(C0-C8)-alkylene-H, CF3, OCF3, OCF2-CHF2, (C6-C10)-aryl, O—(C6-C10)-aryl, O—(C1-C4)-alkylene-(C6-C10)-aryl, NO2, COOR$^9$, CONR$^{10}$R$^{11}$, SH, or NR$^{10}$R$^{11}$, where aryl is unsubstituted or mono-, di- or trisubstituted by F, Cl, Br, I, (C1-C4)-alkyl, O—(C1-C4)-alkyl or CF3;
where
$R^9$ is H, Li, Na, K, ½Mg, ½Ca, ammonium ions which are unsubstituted or mono-, di- or trisubstituted by (C1-C4)-alkyl, or is (C1-C8)-alkyl,
$R^{10}$ and $R^{11}$ are each independently H, (C1-C5)-alkyl, phenyl or CH$_2$-phenyl,
where phenyl is unsubstituted or mono-, di- or trisubstituted by F, Cl, Br, I, (C1-C4)-alkyl, O—(C1-C4)-alkyl or CF3;
or
$R^{10}$ and $R^{11}$ together are (C4-C5)-alkylene, in which one CH$_2$ group may be replaced by O, S, NH, N—CH$_3$ or N-benzyl.

The invention more preferably also relates to a process for preparing the compounds of the formula IV in which:
W=CH;
o=1;
$R^1$=H;
$R^2$=H, CH$_3$, OCH$_3$, Br or Cl;
$R^3$=H, CH$_3$, OCH$_3$, Br or Cl;
$R^4$=CH$_3$, CH$_2$CH$_3$ or CH(CH$_3$)$_2$;
$R^5$=H, CH$_3$, CH$_2$CH$_3$ or CH(CH$_3$)$_2$;
$R^6$=H, CH$_3$, CH$_2$CH$_3$ or CH(CH$_3$)$_2$;
$X^3$=Cl, CH$_3$SO$_3$ or p-CH$_3$—C$_6$H$_4$—SO$_3$ and
n2=0 or 1.

The unsubstituted or substituted ammonium ions in the definition of $R^9$ are preferably each triethylammonium.

In particular, the invention relates to a process for preparing compounds of the formula VIII,

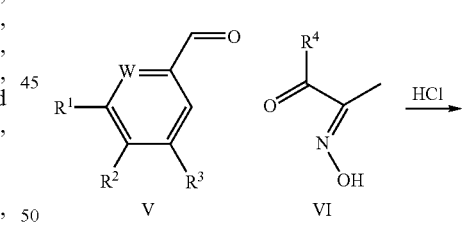

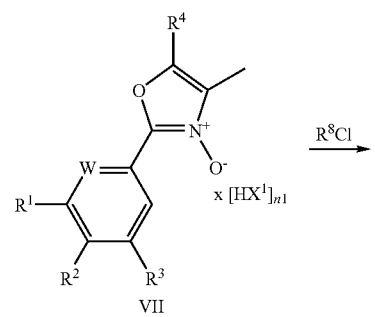

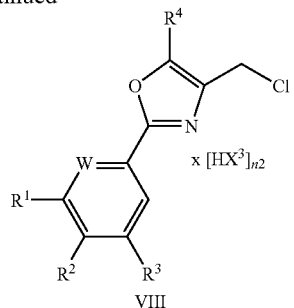

in which
R¹=H,
R²=H or CH₃,
R³=H or OCH₃,
R⁴=CH₃ or CH(CH₃)₂,
W=CH,
X³=Cl or CH₃SO₃ and
n2=0 or 1.

The invention most preferably relates to a process in which the reagent $R^8X^2$ has the structure:

SOCl—Cl, SOBr—Br, CH₃SO₂—Cl or p-CH₃—C₆H₄—SO₂—Cl.

In particular, the invention relates to a process in which the reagent $R^8X^2$ has either the structure SOCl—Cl (formula IX) or CH₃SO₂—Cl (formula X).

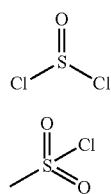

The N-oxide (formula III) may either be isolated or further reacted directly in solution.

When the N-oxide (formula III) or the oxazole (formula IV) is obtained as the salt (n1≠0 or n2≠0), it can be converted to the corresponding free base by treatment with a base such as aqueous solutions of sodium hydroxide, potassium hydroxide, sodium carbonate, potassium carbonate, sodium hydrogencarbonate and potassium hydrogencarbonate, for example.

For the reaction to form the N-oxides (formula I+formula II→formula III), useful reagents HX¹ are hydrogen halides, sulfuric acid and its acidic salt, phosphoric acid and its acidic salts, trifluoroacetic acid, trichloroacetic acid, trifluoromethanesulfonic acid, methanesulfonic acid, benzenesulfonic acid, p-toluenesulfonic acid, formic acid and also HMSO₄, H₂MPO₄, HM₂PO₄ where M=Na, K, preference being given to hydrogen halides. In a particularly preferred embodiment, hydrogen chloride will be selected. In the case of sulfuric acid, hydrogen sulfates (n1=1) or sulfates (n1=½) can form; in the case of phosphoric acid, dihydrogenphosphates (n1=1), hydrogenphosphates (n1=½) or phosphates (n1=⅓) can form.

The reagent HX¹ can be used in stoichiometric amounts, based on the α-ketoxime (formula II), up to a high excess. A preferred working range is the use of stoichiometric amounts up to a 7-fold excess. Particular preference is given to a 1 to 6-fold excess.

For the reaction to form the N-oxides (formula I+formula II→formula III), the solvents used may be protic polar solvents such as carboxylic acids, aprotic dipolar solvents such as sulfoxides, nitriles or ethers or polyethers, aprotic polar solvents such as halogenated aromatic and aliphatic hydrocarbons, or aprotic nonpolar solvents such as aromatic and aliphatic hydrocarbons, or a mixture of the solvent groups. For example, useful solvents are formic acid, glacial acetic acid, propionic acid, N,N-dimethylformamide, N,N-dimethylacetamide, N-methylpyrrolidone, dimethyl sulfoxide, tetrahydrofuran, diethyl ether, diisopropyl ether, tert-butyl methyl ether, ethylene glycol dimethyl ether and higher homologs or dichloromethane and chlorobenzene or toluene, cyclohexane and n-heptane, in each case alone or in a mixture. In a preferred form, the reaction is carried out in glacial acetic acid, in a mixture of glacial acetic acid and ethylene glycol dimethyl ether, or in a mixture of glacial acetic acid and toluene.

The reaction temperatures for the formation of the N-oxides (formula I+formula II→formula II) can be varied within a wide range and depend upon factors including the solubility properties of the aldehydes (formula I) and α-ketoximes (formula II) to be converted. Thus, in principle, reaction temperatures of from minus 20° C. to 150° C. are possible, preference being given in general to reaction temperatures of from minus 10° C. to 90° C. In a particularly preferred embodiment, reaction temperatures of from 0° C. to 60° C. will be selected.

The formation of the N-oxides (formula I+formula II→formula II) can be carried out either in a closed system under elevated pressure or else in an open system under standard pressure, i.e., for example, by introducing a hydrogen halide gas into the system open to the atmosphere or by using a hydrogen halide gas in an organic solvent.

When a further function such as COOR⁹ which can react with activated acid derivatives is present among the R¹ to R⁶ radicals, the product can be obtained as the acid derivative COX² or, after preceding hydrolysis by processes known in principle, as the free acid COOH by acidic or alkaline hydrolysis.

The reagent $R^8X^2$ may be used in stoichiometric amounts, based on the intermediate N-oxide (formula III), up to a high excess. Preferably, the amount used is in stoichiometric amounts in a range is the use of amounts up to a 5-fold excess. Particular preference is given to a 1-4-fold excess. This introduces the X² moiety (of $R^3X^2$) in formula IV in covalently bonded form and converts R⁸ to HX³ by hydrolysis.

For the reaction for the formation of the halomethyloxazoles (formula III→formula IV), the solvents used may be aprotic dipolar solvents such as amides, sulfoxides, nitriles or ethers or polyethers, aprotic polar solvents such as halogenated aromatic and aliphatic hydrocarbons, or aprotic nonpolar solvents such as aromatic and aliphatic hydrocarbons, or a mixture of the solvent groups. For example, useful solvents are N,N-dimethylformamide, N,N-dimethylacetamide, N-methylpyrrolidone, dimethyl sulfoxide, tetrahydrofuran, diethyl ether, diisopropyl ether, tert-butyl methyl ether, ethylene glycol dimethyl ether and higher homologs, or dichloromethane and chlorobenzene or toluene, cyclohexane and n-heptane, in each case alone or in a mixture. In a preferred form, the reaction is carried out in dichloromethane or toluene. The reaction may also be carried out without solvent in an excess of the thionyl chloride or methanesulfonyl chloride reagents.

The reaction temperatures for the formation of the halomethyloxazoles (formula III→formula IV) can be varied within a wide range and depend upon factors including the solubility properties for the aldehydes and α-ketoximes to be converted.

Thus, in principle, reaction temperatures from minus 20° C. to 150° C. are possible, preference being given generally to reaction temperatures of from 20° C. to 120° C. In a particularly preferred embodiment, reaction temperatures of from 20° C. to 80° C. will be selected.

Halogen represents fluorine, chlorine, bromine or iodine, preferably fluorine, chlorine, bromine, more preferably chlorine or bromine, and most preferably chlorine.

An alkyl radical is understood to mean a straight-chain or branched hydrocarbon chain having from one to six carbons, for example methyl, ethyl, propyl, butyl, pentyl, hexyl, isopropyl, isobutyl, neopentyl, tert-butyl.

The alkyl radicals may be mono-, di- or trisubstituted by suitable groups, for example: F, Cl, Br, I, CF3, NO2, N3, CN, COOH, COO(C1-C6)-alkyl, CONH2, CONH(C1-C6)-alkyl, CON[(C1-C6)-alkyl]2, (C3-C8)-cycloalkyl, (C2-C6)-alkenyl, (C2-C6)-alkynyl, (C6-C10)-aryl.

An aryl radical is understood to mean a phenyl, naphthyl, biphenyl, tetrahydronaphthyl, alpha- or beta-tetralonyl, indanyl or indan-1-onyl radical.

The aryl radicals may be mono-, di- or trisubstituted by suitable groups, for example: F, Cl, Br, I, CF3, NO2, SF5, N3, CN, COOH, COO(C1-C6)-alkyl, CONH2, CONH(C1-C6)-alkyl, CON[(C1-C6)alkyl]2, (C3-C8)-cycloalkyl, (C1-C10)-alkyl, (C2-C6)-alkenyl, (C2-C6)-alkynyl, O—(C1-C6)-alkyl, O—CO—(C1-C6)-alkyl, O—CO—(C6-C10)-aryl.

A cycloalkyl radical is understood to mean a three- to eight-membered ring system which contains one or more rings and is present in saturated or partially unsaturated (with one or two double bonds) form which is composed exclusively of carbon atoms, for example cyclopropyl, cyclopentyl, cyclopentenyl, cyclohexyl or adamantyl.

The cycloalkyl radicals may be mono-, di- or trisubstituted by suitable groups, for example: F, Cl, Br, I, CF3, NO2, N3, CN, COOH, COO(C1-C6)-alkyl, CONH2, CONH(C1-C6)-alkyl, CON[(C1-C6)alkyl]2, (C3-C8)-cycloalkyl, (C1-C10)-alkyl, (C2-C6)-alkenyl, (C2-C6)-alkynyl, O—(C1-C6)-alkyl, O—CO—(C1-C6)-alkyl, O—CO—(C6-C10)-aryl.

A heteroaryl radical is understood to mean a C5-C6-heterocycle which may contain from 1 to 4 heteroatoms from the group O, N, S. Examples include furan, thiophene, pyrrole, pyridine, pyrazine, pyrimidine, pyridazine, oxazole, isoxazole, thiazole, isothiazole, furazan, tetrazole.

The inventive compounds of the formula IV can be reacted, for example, according to DE 102004040736.3 further to give pharmaceutically active substances, the PPAR agonists.

EXAMPLE 1

2-(3-Methoxyphenyl)-4,5-dimethyloxazole 3-oxide (formula XI)

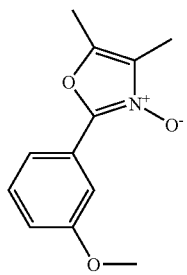

15.2 g (0.150 mol) of 2,3-butanedione monoxime were initially charged and 260 ml of toluene, 22.1 g (0.157 mol) of 3-methoxybenzaldehyde and 70 ml (73.4 g, 1.224 mol) of glacial acetic acid were added with stirring. 27.3 g (0.749 mol) of hydrogen chloride gas were introduced with cooling at such a rate that the internal temperature was <22° C. Subsequently, the mixture was stirred for up to 16 h. With stirring, the reaction mixture was added to 600 ml of water (exothermic reaction). The pH was adjusted to 10.6, for which 172 ml (1.930 mol) of 33% aqueous sodium hydroxide solution were required; the internal temperature was kept <32° C. by external cooling. Two phases formed and were separated. The aqueous phase was extracted twice with 100 ml each time of toluene and subsequently discarded. The combined organic phases were concentrated under reduced pressure while distilling off 50 ml. The thus obtained toluenic solution (420 ml) was used directly for the synthesis of 4-chloromethyl-2-(3-methoxyphenyl)-5-methyloxazole hydrochloride.

Yield: 32.9 g (100%) of 2-(3-methoxyphenyl)-4,5-dimethyloxazole 3-oxide, Not isolated, assumption for the calculation of the subsequent stage. The data which follow were measured on the pure substance which was obtained after the solvent of the organic phases had been distilled off completely.

Melting point: 114° C.

$^1$H NMR (CDCl$_3$, 400 MHz) δ (ppm)=2.20 (s, 3H); 2.35 (s, 3H); 3.87 (s, 3H); 6.98 (m, 1 H); 7.38 (m, 1 H); 7.88 (m, 3 H); 8.26 (m, 1 H).

EXAMPLE 2

4-Chloromethyl-2-(3-methoxyphenyl)-5-methyloxazole hydrochloride (formula XII)

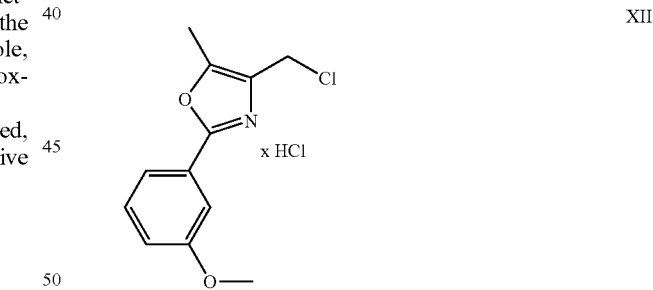

The entire toluenic solution from Example 1 (420 ml) was admixed at 60° C. dropwise with 54.2 g (0.456 mol) of thionyl chloride and stirred at <60° C. for up to 22 h. Subsequently, the mixture was concentrated by distilling off 229 ml. The suspension was cooled to <20° C., and the product was isolated by filtration with suction, washed 3 times with 20 ml each time of toluene and dried at elevated temperature under reduced pressure.

Yield: 23.2 g (56%) of 4-chloromethyl-2-(3-methoxyphenyl)-5-methyloxazole hydrochloride Melting point: 117° C.

$^1$H NMR (CDCl$_3$, 400 MHz) δ (ppm)=2.58 (s, 3H); 3.92 (s, 3 H); 4.78 (s, 2 H); 7.15 (m, 1 H); 7.42 (m, 1 H); 7.79 (m, 1 H); 8.04 (m, 1 H).

EXAMPLE 3

4-Chloromethyl-2-(3-methoxyphenyl)-5-methyloxazole (formula XIII)

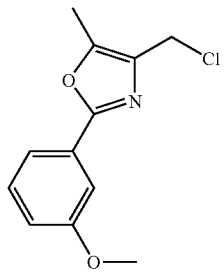

XIII 10.1 g (0.037 mol) of 4-chloromethyl-2-(3-methoxyphenyl)-5-methyloxazole hydrochloride were suspended in 100 ml of water and 75 ml of dichloromethane. With stirring, a pH of 12 was established in the water phase with 45 ml (0.023 mol) of aqueous sodium hydroxide solution. Subsequently, the phases were separated and the aqueous phase was discarded. The organic phase was concentrated by distillation completely under reduced pressure. The remaining oil crystallized through after the addition of seed crystals.

Yield: 8.0 g (92%) of 4-chloromethyl-2-(3-methoxyphenyl)-5-methyloxazole

Melting point: 46-50° C.

$^1$H NMR (CDCl$_3$, 400 MHz) δ (ppm)=2.43 (s, 3 H); 3.88 (s, 3 H); 4.56 (s, 2 H); 6.99 (m, 1 H); 7.35 (m, 1 H); 7.54 (m, 1 H); 7.60 (m, 1H).

EXAMPLE 4

4,5-Dimethyl-2-p-tolyloxazole 3-oxide hydrochloride (formula XIV)

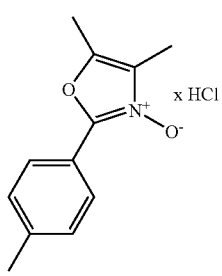

XIV 100 g (979 mmol) of butane-2,3-dione monoxime were initially charged and dissolved in 500 ml of acetic acid. 120 g (979 mmol) of 4-methylbenzaldehyde were added. 100 g (2.74 mol) of hydrogen chloride gas were introduced at such a rate that an internal temperature of 40° C. was not exceeded. Subsequently, the mixture was stirred at 35-40° C. for a further 2-3 hours. With intensive cooling, 2 l of tert-butyl methyl ether were added. The reaction mixture was stirred at 10° C. for 1 hour. The product was isolated by filtration with suction, washed with tert-butyl methyl ether and dried at elevated temperature under reduced pressure.

Yield: 213 g (91%) of 4,5-dimethyl-2-p-tolyloxazole 3-oxide hydrochloride

Melting point: 101° C.

$^1$H NMR (DMSO-D$_6$, 500 MHz) δ (ppm)=10.30 (s$_{br}$, 1H), 8.17 (d, J=8.3 Hz; 2H), 7.47 (d, J=8.3 Hz; 2H), 2.44 (s, 3H), 2.42 (s, 3H)

EXAMPLE 5

4-Chloromethyl-5-methyl-2-p-tolyloxazole (formula XV)

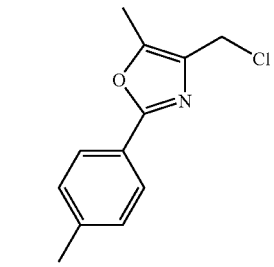

XV 32.8 g (137 mmol) of 4,5-dimethyl-2-p-tolyloxazole 3-oxide hydrochloride were suspended in 165 ml of dichloromethane. 17.5 g (151 mmol) of methanesulfonyl chloride were added. The reaction was stirred at reflux up to full conversion (HPLC). Subsequently, 200 ml of ethylene glycol dimethyl ether were added, and the dichloromethane was distilled off under reduced pressure. The reaction mixture was cooled to 15° C. and 250 ml of water were added. The mixture was stirred at 15° C. for 1 hour. The precipitated product was isolated by filtration with suction, washed with water and dried at elevated temperature under reduced pressure.

Yield: 27.6 g (91%) of 4-chloromethyl-5-methyl-2-p-tolyloxazole

Melting point: 95° C.

$^1$H NMR (DMSO-D$_6$, 500 MHz) δ (ppm)=7.82 (d, J=8.1 Hz, 2H), 7.33 (d, J=8.1 Hz, 2H), 4.74 (s, 2H), 2.43 (s, 3H), 2.37 (s, 3H)

EXAMPLE 6

4-Methylpentane-2,3-dione 2-oxime (formula XVI)

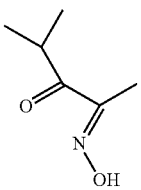

XVI 100 g (948 mmol) of 2-methylpentan-3-one were dissolved in 400 ml of tert-butyl methyl ether. 50 g (274 mmol) of solution of hydrochloride in ethylene glycol dimethyl ether (20%) were added. Subsequently, a solution of 117 g (949 mmol) isoamyl nitrite in 150 ml of tert-butyl methyl ether was added dropwise within 60 minutes. The solvent was removed fully under reduced pressure. The residue was taken up in 300 ml of n-heptane and concentrated again under reduced pressure. After 200 ml of n-heptane had been added, extraction was effected with 522 ml of sodium hydroxide solution (2 molar). After phase separation, the aqueous phase was washed with n-heptane. The aqueous phase was acidified by adding conc. hydrochloric acid. The product was isolated by filtration with suction, washed with water and dried at elevated temperature under reduced pressure.

Yield: 61.1 g (50%) of 4-methylpentane-2,3-dione 2-oxime

Melting point: 94° C.

$^1$H NMR (DMSO-D$_6$, 500 MHz) δ (ppm)=12.3 (s, 1H), 3.54 (sept, J=6.9 Hz, 1H), 1.82 (2, 3H), 1.02 (s, 3H), 1.01 (s, 3H).

EXAMPLE 7

5-Isopropyl-2-(3-methoxyphenyl)-4-methyloxazole 3-oxide (formula XVII)

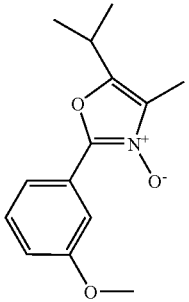

XVII 19.0 g (137 mmol) of 3-methoxybenzaldehyde were added to a solution of 18.0 g (137 mmol) of 4-methylpentane-2,3-dione 2-oxime in 30 g (99 mmol) of solution of hydrogen chloride in acetic acid (12%) and 30 g (164 mmol) of solution of hydrogen chloride in ethylene glycol dimethyl ether (20%). The reaction was stirred at 50-55° C. for 3 hours and at room temperature for 60 hours. Subsequently, 500 ml of water and 300 ml of tert-butyl methyl ether were added before a pH of 3-4 was established by adding sodium hydrogen carbonate. After phase separation, the aqueous phase was extracted twice with 100 ml each time of tert-butyl methyl ether. The combined organic phases were washed with 4×100 ml of water and concentrated fully under reduced pressure.

Yield: 42.8 g (79% purity) (100%) of 5-isopropyl-2-(3-methoxyphenyl)-4-methyloxazole 3-oxide $^1$H NMR (DMSO-D$_6$, 500 MHz) δ (ppm)=8.12 (m, 1H), 7.86 (d, J=8.0 Hz, 1H), 7.48 (t, J=8.0 Hz, 1H), 7.06 (dd, J=2.4, 8.0 Hz, 1H), 3.82 (s, 3H), 3.16 (sept, J=7.0 Hz, 1H), 2.12 (s, 3H), 1.29 (d, J=7.0 Hz, 3H).

EXAMPLE 8

4-Chloromethyl-5-isopropyl-2-(3-methoxyphenyl) oxazole (formula XVIII)

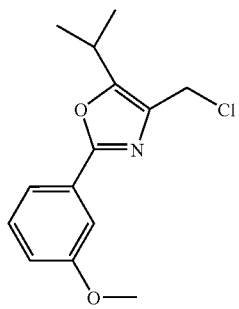

XVIII 75 g (648 mmol) of methanesulfonyl chloride were added at a temperature of 20° C. to a solution of 135 g (435 mmol) of 5-isopropyl-2-(3-methoxyphenyl)-4-methyloxazole 3-oxide in 500 ml of dichloromethane. The reaction was stirred at 40-45° C. up to full conversion. 500 ml of tert-butyl methyl ether and 300 ml of water were added. Addition of 20% sodium hydroxide solution established a pH of 8. After phase separation, the organic phase was washed with 3×200 ml of water. The organic phase was concentrated fully under reduced pressure.

Yield: 132 g (87% purity) (99%) of 4-chloromethyl-5-isopropyl-2-(3-methoxyphenyl)-oxazole $^1$H NMR (DMSO-D$_6$, 500 MHz) δ (ppm)=7.55 (m, 1H), 7.45 (m, 2H), 7.10 (ddd, J=0.9, 2.7, 5.6 Hz, 1H), 4.77 (s, 2H), 3.85 (s, 3H), 3.33 (sept, 7.0 Hz, 1H), 1.30 (d, J=7.0 Hz, 6H).

What is claimed is:

1. A process for preparing a compounds of formula IV,

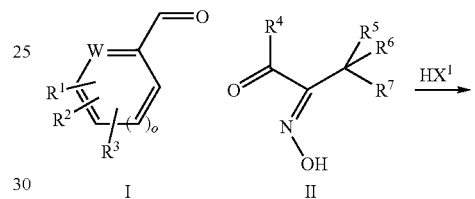

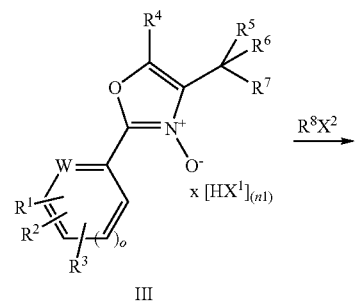

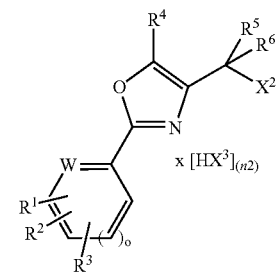

IV comprising reacting an aromatic aldehyde of formula I with an α-ketoxime of formula II
wherein:
R¹ is selected from the group consisting of H, (C1-C6)-alkyl, F, Cl, Br, I, O—(C0-C8)-alkylene-H, CF₃, OCF₃, SCF₃, SF₅, OCF₂—CHF₂, (C6-C10)-aryl, O—(C6-C10)-aryl, O—(C1-C4)-alkylene-(C6-C10)-aryl, NO₂, COOR⁹, CONR¹⁰R¹¹, SH, and NR¹⁰R¹¹, wherein the aryl moiety is unsubstituted or mono-, di- or tri-substituted by F, Cl, Br, I, (C1-C4)-alkyl, O—(C1-C4)-alkyl or CF₃;

R⁹ is selected from the group consisting of H, (C1-C8)-alkyl, or a Li, Na, K, ½Mg, ½Ca, or ammonium ion wherein the ammonium ion is unsubstituted or mono-, di- or trisubstituted by (C1-C4)-alkyl;

R¹⁰ and R¹¹ are each independently selected from the group consisting of H, (C1-C5)-alkyl, phenyl and CH₂-phenyl,
wherein the phenyl moiety is unsubstituted or mono-, di- or tri-substituted by F, Cl, Br, I, (C1-C4)-alkyl, O—(C1-C4)-alkyl or CF₃;
or
R¹⁰ and R¹¹ taken together are (C4-C5)-alkylene, in which one CH₂ group may be replaced by O, S, NH, N—CH₃ or N-benzyl;

R² is selected from the group consisting of H, (C1-C6)-alkyl, F, Cl, Br, I, O—(C1-C8)-alkylene-H, CF₃, OCF₃, SCF₃, SF₅, OCF₂—CHF₂, (C6-010)-aryl, O—(C6-C10)-aryl, O—(C1-C4)-alkylene-(C6-C10)-aryl, NO₂, COOR⁹, CONR¹⁰R¹¹, SH, and NR¹⁰R¹¹, wherein the aryl moiety is unsubstituted or mono-, di- or trisubstituted by F, Cl, Br, I, (C1-C4)-alkyl, O—(C1-C4)-alkyl or CF₃, and R⁹, R¹⁰ and R¹¹ are each as defined above;

R³ is selected from the group consisting of H, (C1-C6)-alkyl, F, Cl, Br, I, O—(C0-C8)-alkylene-H, CF₃, OCF₃, SCF₃, SF₅, OCF₂—CHF₂, (C6-C10)-aryl, O—(C6-C10)-aryl, O—(C1-C4)-alkylene-(C6-C10)-aryl, NO₂, COOR⁹, CONR¹⁰R¹¹, SH, and NR¹⁰R¹¹, wherein the aryl moiety is unsubstituted or mono-, di- or tri-substituted by F, Cl, Br, I, (C1-C4)-alkyl, O—(C1-C4)-alkyl or CF₃, and R⁹, R¹⁰ and R¹¹ are each as defined above;

W is CH, N, if o=1;
W is O, S, NR12, if o=0;
o is 0 or 1;
R12 is H, (C1-C6)-alkyl, (C1-C6)-alkylenephenyl, or phenyl;
R⁴ is selected from the group consisting of H, COOR⁹, CONR(10)R(11), (C1-C8)-alkyl, (C3-C8)-cycloalkyl, (C1-C3)-alkylene-(C3-C8)-cycloalkyl, phenyl, (C1-C3)-alkylenephenyl, (C5-C6)-heteroaryl, (C1-C3)-alkylene-(C5-C6)-heteroaryl or (C1-C3)-alkyl wherein the (C1-C3)-alkyl is fully or partly substituted by F, and R⁹, R¹⁰ and R¹¹ are each as defined above;

R⁵ and R⁶ are each independently selected from the group consisting of
H, (C1-C8)-alkyl, F, Cl, Br, I, O—(C0-C8)-alkylene-H, O—(C6-C10)-aryl, O—(C1-C4)-alkylene-(C6-C10)-aryl, COOR⁹, CONR¹⁰R¹¹, SH and NR¹⁰R¹¹, and R⁹, R¹⁰, R¹¹ are each as defined above,
or
R⁵ and R⁶ taken together are (C4-C5)-alkylene, in which one CH₂ group may be replaced by O, S, NH, N—CH₃ or N-benzyl; and R⁷ is in the presence of one or more acids HX¹ selected from the group consisting of HCl, HBr, H₂SO₄, H₃PO₄, HOOCCF3, HOOCCCl₃, HO₃SCF₃, HO₃SCH₃, HO₃SC₆H₅, HO₃S—C₆H₄-p-CH₃, HOOCH, to get an N-oxide of formula III

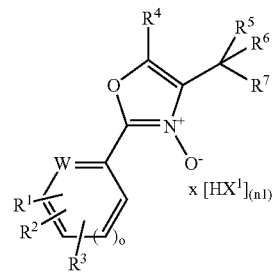

wherein R¹, R², R³, R⁴, R⁵, R⁶, R⁷ and X¹ are each as defined above and
n1 is 0, 1, ½ or ⅓;
and reacting the N-oxide of formula III with the reagent R⁸X² which is a compound selected from the group consisting of SOCl—Cl, SOBr—Br, CH₃SO₂—Cl, CF₃SO₂—Cl, C₆H₅SO₂—Cl, p-CH₃—C₆H₄—SO₂—Cl, CH₃SO₂—O₃SCH₃, CF₃SO₂—O₃SCF₃, C₆H₅SO₂—O₃SC₆H₅ or p-CH₃—C₆H₄—SO₂—O₃S—C₆H₄-p-CH₃,
to yield the compound of formula IV

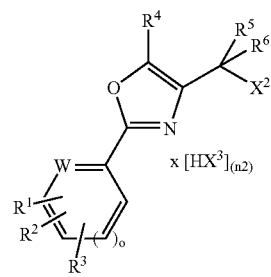

wherein R¹, R², R³, R⁴, R⁵, and R⁶ are each as defined above,
X² is Br, Cl, CH₃SO₃, CF₃SO₃, C₆H₅SO₃ or p-CH₃—C₆H₄—SO₃,
X3 is Cl, Br, CH₃SO₃, CF₃SO₃, C₆H₅SO₃ or p-CH₃—C₆H₄—SO₃ and
n2 is 0 or 1.

2. The process according to claim 1, wherein:
W=CH and
o=1.

3. The process according to claim 2, wherein:
R¹ is H.

4. The process according to claim 3 wherein:
R² is H.

5. The process according to claim 1, wherein:
W=CH;
o=1;
R¹=H;
R²=H, CH₃, OCH₃, Br or Cl;
R³=H, CH₃, OCH₃, Br or Cl;
R⁴=CH₃, CH₂CH₃ or CH(CH₃)₂;
R⁵=H, CH₃, CH₂CH₃ or CH(CH₃)₂;
R⁶=H, CH₃, CH₂CH₃ or CH(CH₃)₂;
X³=Cl, CH₃SO₃ or p-CH₃—C₆H₄—SO₃ and
n2=0 or 1.

6. The process according to claim 1, wherein the compound of formula IV is a compound of formula VIII

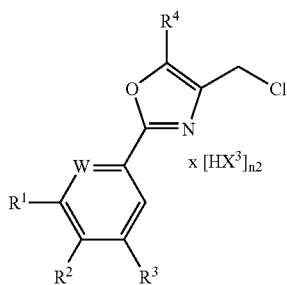

VIII

Wherein:
$R^1$=H,
$R^2$=H or $CH_3$,
$R^3$=H or $OCH_3$,
$R^4$=$CH_3$ or $CH(CH_3)_2$, a
W=CH,
$X^3$=Cl or $CH_3SO_3$, and
n2=0 or 1.

7. The process according to claim 6, wherein the reaction temperature for forming the N-oxides of formula III by the reaction of compounds of formulae I and II is between about −20° C. and +150° C.

8. The process according to claim 7, wherein the reaction for forming the N-oxides of formula III is carried out in aprotic, polar, or aprotic nonpolar solvent or a mixture thereof.

9. The process according to claim 6, wherein the reaction temperature for forming the compound of formula IV from the compound of formula III is from about −20° C. to +150° C.

10. The process according to claim 9, wherein the reaction for forming the compound of formula IV is carried out in an aprotic dipolar, aprotic polar or aprotic non-polar solvent or a mixture thereof.

11. The process according to claim 10, wherein the compound of the formula $R^8X^2$ is used in an amount of from about a 1 to 4-fold excess based on the amount of the N-oxide of formula III.

* * * * *

UNITED STATES PATENT AND TRADEMARK OFFICE
CERTIFICATE OF CORRECTION

PATENT NO. : 7,544,809 B2
APPLICATION NO. : 11/754477
DATED : May 29, 2007
INVENTOR(S) : Holla et al.

It is certified that error appears in the above-identified patent and that said Letters Patent is hereby corrected as shown below:

Column 15, line 64 reads:

"R7 is in the presence of one or more acids HX1 selected", and should read

--R7 is H; in the presence of one or more acids HX1 selected--

Signed and Sealed this

Twenty-fifth Day of August, 2009

David J. Kappos
*Director of the United States Patent and Trademark Office*